US008568484B2

(12) United States Patent
Robie

(10) Patent No.: US 8,568,484 B2

(45) Date of Patent: Oct. 29, 2013

(54) SPINAL IMPLANT

(75) Inventor: Bruce Robie, Glen Rock, NJ (US)

(73) Assignee: Zimmer Spine, Inc., Minneapolis, MN (US)

(*) Notice: Subject to any disclaimer, the term of this patent is extended or adjusted under 35 U.S.C. 154(b) by 0 days.

(21) Appl. No.: 13/479,778

(22) Filed: May 24, 2012

(65) Prior Publication Data

US 2012/0303123 A1 Nov. 29, 2012

Related U.S. Application Data

(60) Continuation of application No. 11/770,087, filed on Jun. 28, 2007, now Pat. No. 8,192,492, which is a division of application No. 29/277,225, filed on Feb. 19, 2007, now Pat. No. Des. 566,842.

(51) Int. Cl.
*A61F 2/44* (2006.01)

(52) U.S. Cl.
USPC .......................................................... 623/17.16

(58) Field of Classification Search
USPC ............................................ 623/17.11–17.16
See application file for complete search history.

(56) References Cited

U.S. PATENT DOCUMENTS

| | | | | |
|---|---|---|---|---|
| 229,175 | A | 6/1880 | Payne | |
| D229,175 | S | 11/1973 | Libertone et al. | |
| D283,831 | S | 5/1986 | Maddock | |
| 5,192,327 | A * | 3/1993 | Brantigan | 623/17.11 |
| 5,306,309 | A | 4/1994 | Wagner et al. | |
| 5,522,899 | A | 6/1996 | Michelson | |
| 5,534,028 | A | 7/1996 | Bao et al. | |
| D377,527 | S | 1/1997 | Michelson | |
| 5,607,424 | A * | 3/1997 | Tropiano | 623/17.16 |
| 5,776,199 | A | 7/1998 | Michelson | |
| 5,810,825 | A | 9/1998 | Huebner | |
| 5,888,222 | A | 3/1999 | Coates et al. | |
| 5,989,289 | A | 11/1999 | Coates et al. | |
| 6,066,175 | A * | 5/2000 | Henderson et al. | 623/17.11 |
| 6,096,080 | A | 8/2000 | Nicholson et al. | |
| D433,750 | S | 11/2000 | Burrows | |
| 6,143,033 | A | 11/2000 | Paul et al. | |
| 6,245,108 | B1 * | 6/2001 | Biscup | 623/17.11 |
| 6,371,988 | B1 | 4/2002 | Pafford et al. | |
| 6,423,095 | B1 | 7/2002 | Van Hoeck et al. | |
| 6,425,920 | B1 | 7/2002 | Hamada | |
| 6,447,544 | B1 | 9/2002 | Michelson | |
| 6,458,159 | B1 | 10/2002 | Thalgott | |
| 6,468,311 | B2 | 10/2002 | Boyd et al. | |
| 6,503,279 | B1 | 1/2003 | Webb et al. | |
| 6,520,993 | B2 | 2/2003 | James et al. | |

(Continued)

FOREIGN PATENT DOCUMENTS

| | | | |
|---|---|---|---|
| WO | 9909914 | A1 | 3/1999 |
| WO | 0007528 | A1 | 2/2000 |
| WO | 02091909 | A3 | 8/2003 |

*Primary Examiner* — Mary Hoffman

(74) *Attorney, Agent, or Firm* — Seager, Tufte & Wickhem, LLC

(57) ABSTRACT

A spinal implant as provided having a porous body that includes a leading end, a convex trailing end and first and second sides extending between the leading and trailing ends. At least a portion of the leading end is generally straight. The body further includes a generally dome-shaped superior surface and a generally planar inferior surface. The superior surface is convex between the leading and trailing ends and is convex between the first and second sides.

20 Claims, 3 Drawing Sheets

(56) References Cited

U.S. PATENT DOCUMENTS

| | | | | |
|---|---|---|---|---|
| D472,972 | S | 4/2003 | Anderson | |
| 6,638,310 | B2 | 10/2003 | Lin et al. | |
| 6,733,535 | B2 | 5/2004 | Michelson | |
| 6,746,484 | B1 | 6/2004 | Liu et al. | |
| 6,749,636 | B2 | 6/2004 | Michelson | |
| 6,800,093 | B2 | 10/2004 | Nicholson et al. | |
| D497,993 | S | 11/2004 | Dixon | |
| 6,964,687 | B1 | 11/2005 | Bernard et al. | |
| 7,048,765 | B1 | 5/2006 | Grooms et al. | |
| 7,238,203 | B2 | 7/2007 | Bagga et al. | |
| D553,742 | S | 10/2007 | Park | |
| 7,435,261 | B1 * | 10/2008 | Castro | 623/17.11 |
| 7,749,272 | B2 | 7/2010 | Robie et al. | |
| 2002/0106393 | A1 | 8/2002 | Bianchi et al. | |
| 2003/0023306 | A1 | 1/2003 | Liu et al. | |
| 2003/0109928 | A1 * | 6/2003 | Pasquet et al. | 623/17.11 |
| 2003/0125739 | A1 | 7/2003 | Bagga et al. | |
| 2003/0153975 | A1 * | 8/2003 | Byrd et al. | 623/17.11 |
| 2004/0068320 | A1 | 4/2004 | Robie et al. | |
| 2004/0082999 | A1 * | 4/2004 | Mathys et al. | 623/17.11 |
| 2004/0117020 | A1 * | 6/2004 | Frey et al. | 623/17.11 |
| 2004/0127990 | A1 * | 7/2004 | Bartish et al. | 623/17.11 |
| 2004/0133279 | A1 | 7/2004 | Krueger et al. | |
| 2004/0158324 | A1 * | 8/2004 | Lange | 623/17.11 |
| 2004/0186572 | A1 * | 9/2004 | Lange et al. | 623/17.11 |
| 2004/0199251 | A1 | 10/2004 | McCombe et al. | |
| 2004/0230306 | A1 | 11/2004 | Hoeck et al. | |
| 2004/0230308 | A1 | 11/2004 | Michelson | |
| 2005/0004672 | A1 | 1/2005 | Pafford et al. | |
| 2005/0119753 | A1 | 6/2005 | McGahan et al. | |
| 2005/0149188 | A1 | 7/2005 | Cook et al. | |
| 2005/0171606 | A1 | 8/2005 | Michelson | |
| 2005/0222682 | A1 | 10/2005 | Link et al. | |
| 2005/0240267 | A1 | 10/2005 | Randall et al. | |
| 2005/0251257 | A1 | 11/2005 | Mitchell et al. | |
| 2006/0100705 | A1 | 5/2006 | Puno et al. | |
| 2006/0190082 | A1 | 8/2006 | Keller et al. | |
| 2006/0241763 | A1 | 10/2006 | Paul et al. | |
| 2006/0247772 | A1 | 11/2006 | McKay | |
| 2009/0093883 | A1 * | 4/2009 | Carrasco | 623/17.16 |
| 2010/0152853 | A1 * | 6/2010 | Kirschman | 623/17.11 |

* cited by examiner

SPINAL IMPLANT

CROSS REFERENCE

This application is a continuation of U.S. patent application Ser. No. 11/770,087, filed on Jun. 28, 2007, which is a divisional of U.S. Design patent application Ser. No. 29/277,225, filed Feb. 19, 2007, now U.S. Pat. No. D566,842, issued Apr. 15, 2008, the disclosures of which are expressly incorporated by reference herein in its entirety.

FIELD OF THE INVENTION

The present invention relates generally to skeletal implants. More particularly, the present invention relates to implants for stabilizing intervertebral joints.

BACKGROUND OF THE INVENTION

Chronic back problems cause pain and disability for a large segment of the population. In many cases, chronic back problems are caused by intervertebral disc disease. When an intervertebral disc is diseased, the vertebrae between which the disc is positioned may be inadequately supported, resulting in persistent pain. Stabilization and/or arthrodesis of the intervertebral joint can reduce the pain and debilitating effects associated with disc disease.

Spinal stabilization systems and procedures have been developed to stabilize diseased intervertebral joints and, in some cases, to fuse the vertebrae that are adjacent the diseased joint space. Most fusion techniques include removing some or all of the disc material from the affected joint, and stabilizing the joint by inserting an implant (e.g., a bone graft or other material to facilitate fusion of the vertebrae) in the cleaned intervertebral space.

Spinal implants can be inserted into the intervertebral space through an anterior approach, a lateral (transverse) approach, a posterior approach, or postero-lateral approach. The anterior approach involves a surgeon seeking access to the spine through the front (i.e., abdominal area) of the patient. The posterior approach involves a surgeon seeking access to the spine through the back of the patient. The postero-lateral approach is similar to the posterior approach with access coming more from either or both sides of the patient. A variety of different anterior, posterior and posterior-lateral techniques are known.

SUMMARY OF THE INVENTION

While the invention will be described in connection with certain embodiments, it will be understood that the invention is not limited to these embodiments. On the contrary, the invention includes all alternatives, modifications and equivalents as may be included within the spirit and scope of the present invention.

A spinal implant is provided having a porous body that includes a leading end, a convex trailing end and first and second sides extending between the leading and trailing ends. At least a portion of the leading end is generally straight. The body also includes a generally dome-shaped superior surface and a generally planar inferior surface. The superior surface is convex between the leading and trailing ends and is convex between the first and second sides.

In other embodiments, the implant may include one or more of the following features. The implant may further include a first opening extending through the implant from the superior surface to the inferior surface and a second opening communicating with the first opening and extending through the trailing end. The first and second openings are configured for receipt of an inserter instrument to insert the implant between vertebral bodies.

The inferior surface may have a generally trapezoidal shape. The first and second sides may be generally straight and may diverge away from one another from the leading end to the trailing end. The body may be made of metal. The leading end may be a posterior end and the trailing end may be an anterior end.

BRIEF DESCRIPTION OF THE DRAWINGS

The accompanying drawings, which are incorporated in and constitute a part of this specification, illustrate embodiments of the invention and, together with a general description of the invention given above, and a detailed description of the embodiments given below, serve to explain the principles of the invention.

DETAILED DESCRIPTION

Figure 1:
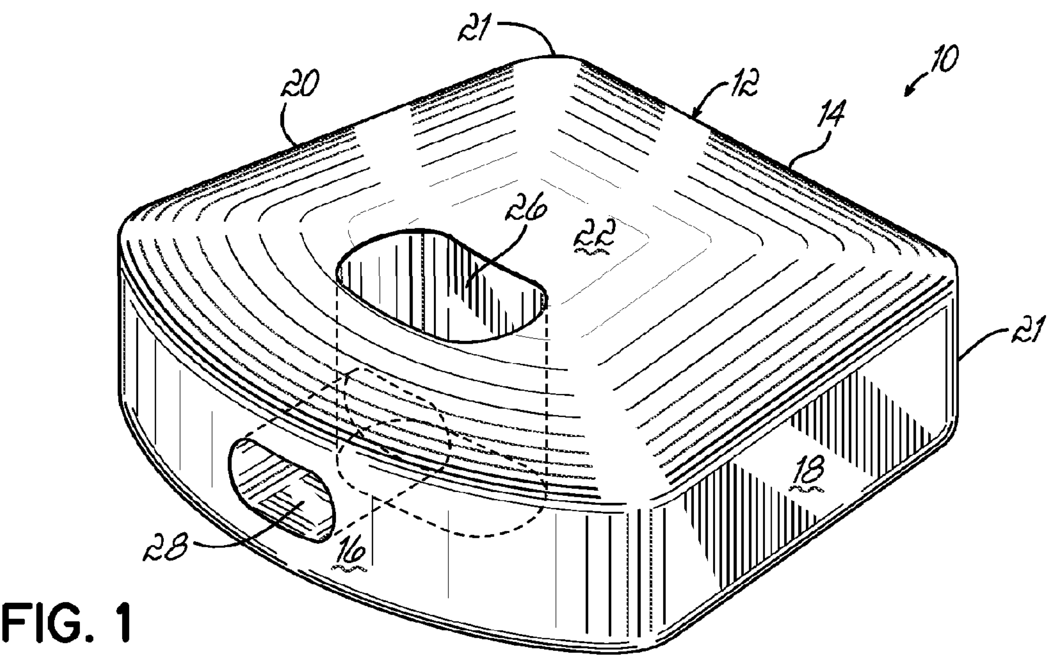
FIG. 1 is a front perspective view of a spinal implant according to one embodiment of the present invention.

The present invention is directed to skeletal implants and methods for placing implants between bones desired to be fused. It is preferred for the implants to be used for vertebral/spinal applications such as fusing cervical, thoracic and/or lumbar intervertebral joints. In the case of fusing an intervertebral joint, implants in accordance with the principles of the present invention can be implanted using an anterior, posterior or postero-lateral approach to the patient's vertebrae.

As used herein, an "implant" includes any implant suitable for facilitating fusion between adjacent bones and includes implants prepared from known implant materials including, non-bone material such as titanium, stainless steel, porous tantalum or other metal, bio-glass, calcium phosphate, ceramic, carbon fiber-based polymers and biodegradable polymers.

FIGS. 1-7 illustrate a spinal implant 10 according to one embodiment of the present invention. Implant 10 includes a body 12 having a leading end 14, a convex trailing end 16 and first 18 and second 20 sides that extend between the leading 14 and trailing 16 ends. Leading end 14 may include rounded, or radiused portions, indicated at 21, that blend with sides 18, 20. Leading end 14 may be generally straight between the rounded portions 21. The body 12 further includes a generally dome-shaped superior surface 22 and an inferior surface 24 that may be generally flat. The superior surface is convex between the leading 14 and trailing 16 ends and is also convex between sides 18, 20. Accordingly, the superior surface is convex in both an anterior-to-posterior direction and a medial-to-lateral direction.

Implant 10 further includes an opening 26 that extends completely through implant 10 from the superior surface 22 to the inferior surface 24. Implant 10 also includes an opening 28 that communicates with opening 26 and extends through the trailing end 16. The function of openings 26, 28 are described below. In an exemplary embodiment, openings 26 and 28 may be generally oval-shaped. However, one or both of openings 26, 28 may have other shapes within the scope of the present invention.

Figure 2:
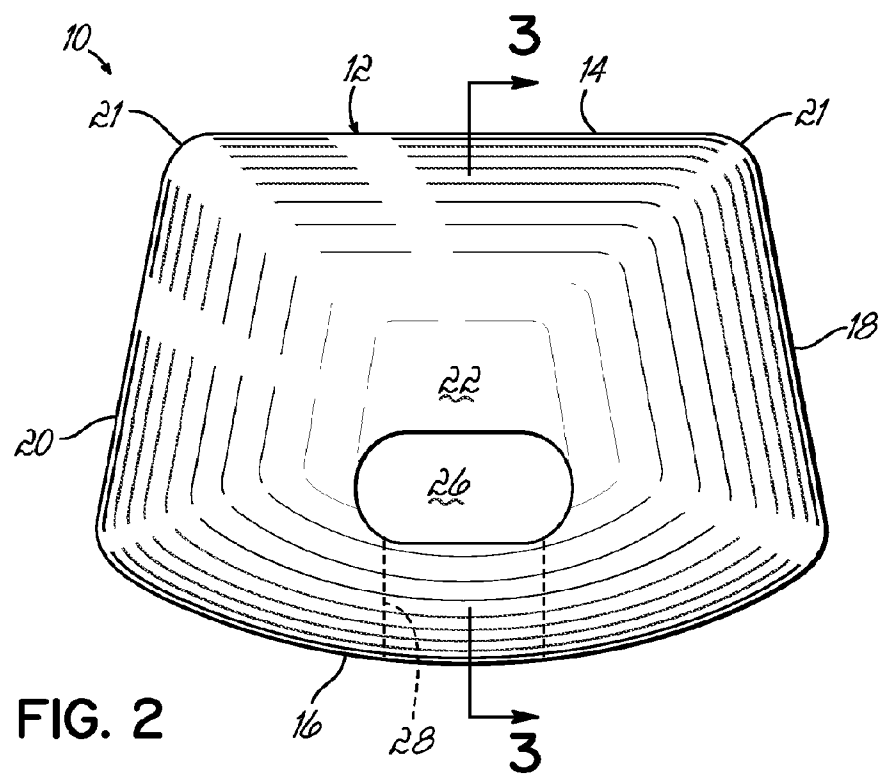
FIG. 2 is a top plan view of the implant shown in FIG. 1.
Figure 3:
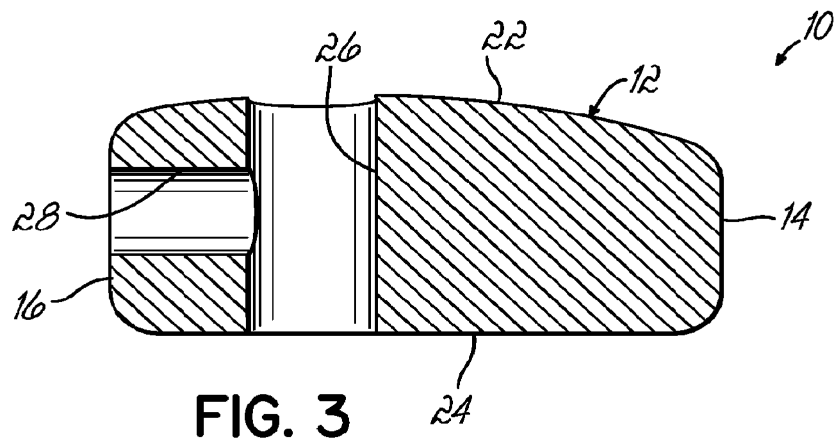
FIG. 3 is a cross-sectional view taken along line 3-3 in FIG. 2.
Figure 4:
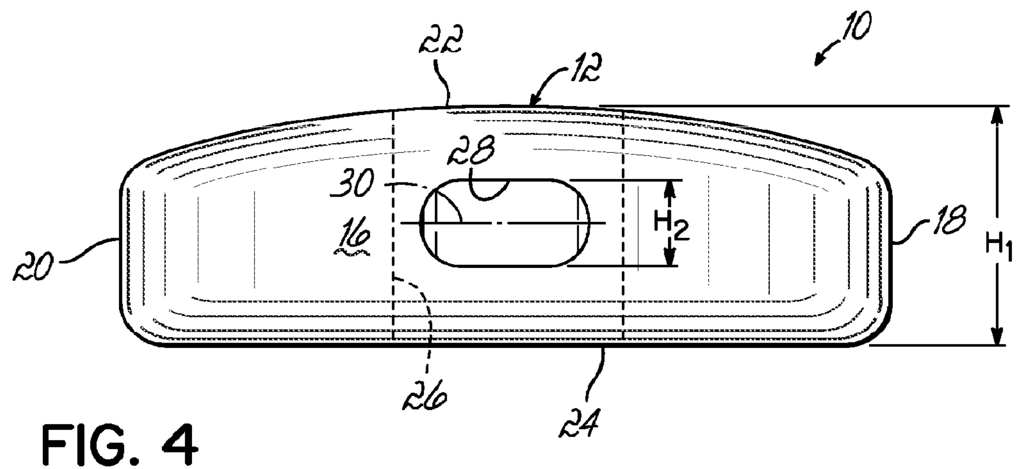
FIG. 4 is a front elevational view of the implant shown in FIGS. 1-3.
Figure 5:
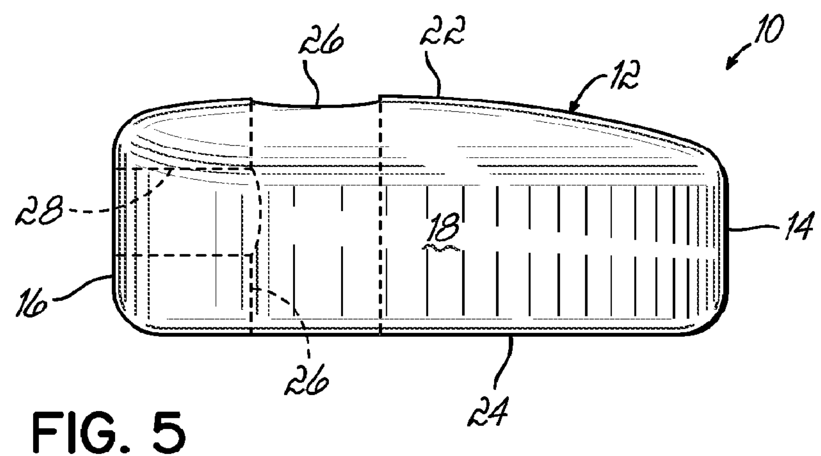
FIG. 5 is a side elevational view of the implant shown in FIGS. 1-4.
Figure 6:
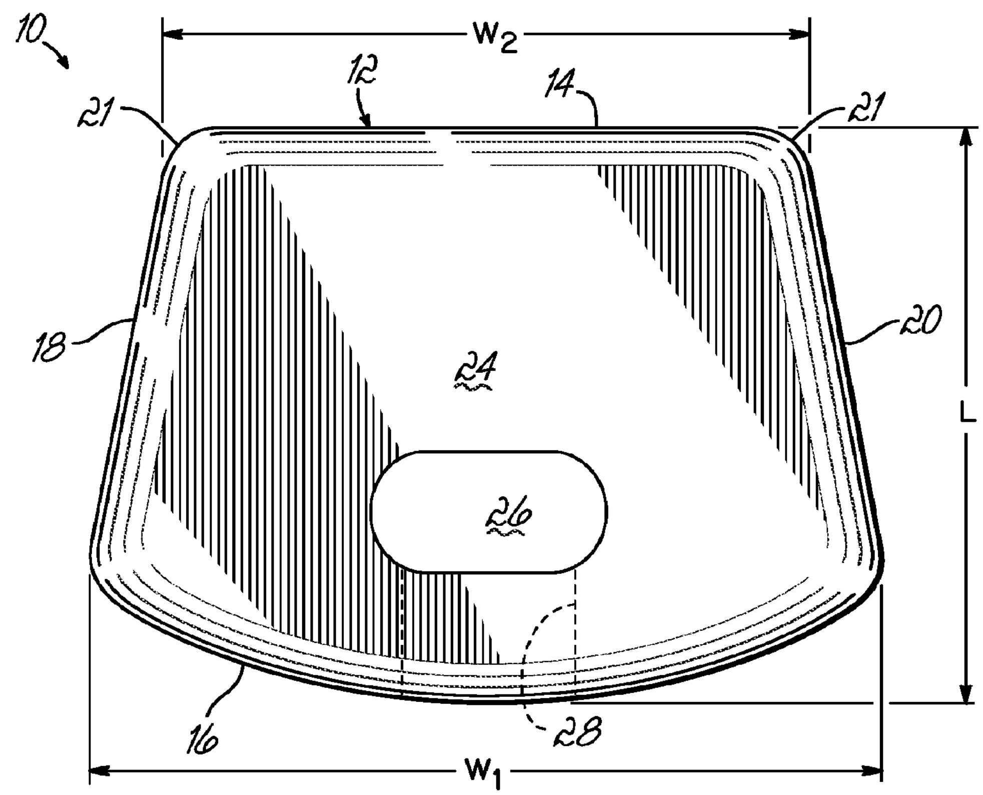
FIG. 6 is a bottom view of the implant shown in FIGS. 1-5.
Figure 7:
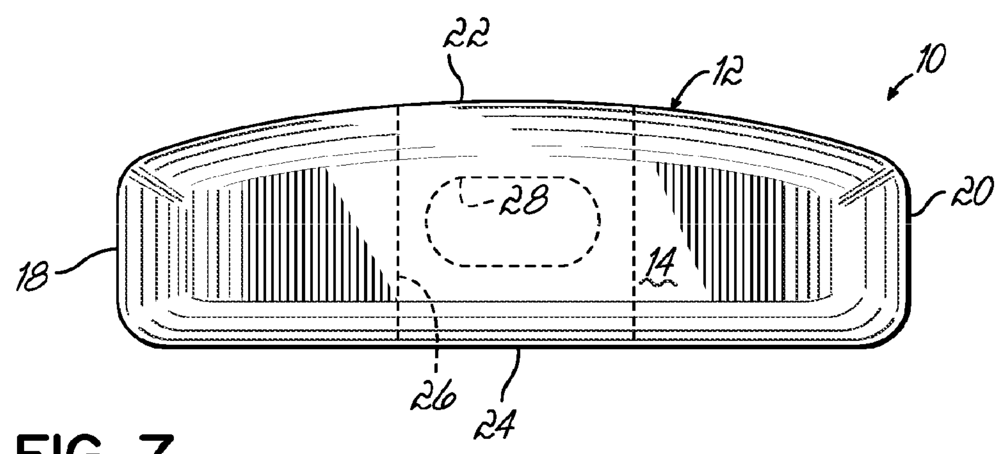
FIG. 7 is a rear elevational view of the implant shown in FIGS. 1-6.

As shown in FIG. 4, implant 10 has a height "H.sub.1" extending between the highest point on the superior surface 22 and the inferior surface 24. Implant 10 also includes length "L" that extends between the leading end 14 and the location on trailing end 16 that is the farthest away from leading end 14. A first width "W.sub.1" exists between sides 18, 20 at the trailing end 16 and a second width "W.sub.2" exists between sides 18, 20 at the leading end 14. Sides 18 and 20 may diverge away from one another between the leading 14 and trailing 16 ends, as shown in FIGS. 2 and 6. Accordingly, the inferior surface 24 has a generally trapezoidal shape and width "W.sub.1" is greater than width "W.sub.2". The magnitudes height "H", length "L" and widths "W.sub.1" and "W.sub.2" may vary with application.

In an exemplary embodiment, implant 10 may be inserted into a cervical disc space to fuse adjacent cervical vertebrae. Also, in an exemplary embodiment, implant 10 may be inserted using an anterior approach, such that leading end 14 is a posterior end and trailing end 16 is an anterior end. In this event, a distal end, or key of an instrument, such as an inserter (not shown) may be inserted into opening 28 such that a width of the key initially extends generally along a longitudinal axis 30 of opening 28. When the inserter is inserted farther into implant 10, the key of the inserter reaches the intersection of openings 26 and 28. The inserter may then be rotated 90 degrees such that the width of the key extends along the length of opening 26 partially between the superior 22 and inferior 24 surfaces. The width of the inserter key is sized such that it is greater than a height "H.sub.2" of opening 28, which releasably secures the inserter to implant 10. The inserter may be removed by rotating it 90 degrees which generally aligns the width of the key with the longitudinal axis 30 of opening 28, and then retracting the inserter from implant 10.

In an exemplary embodiment, when implant 10 is used to fuse adjacent cervical vertebrae, the generally trapezoidal shape of inferior surface 24, including the rounded portions 21 of leading end 14, may match the general shape of cervical vertebral bodies. Also, in this exemplary embodiment, the dome-shaped superior surface 22 may generally match cervical endplate anatomy and the generally flat inferior surface 24 may mate with a flat inferior endplate in the cervical disc space or a surgically-created flat surface of a vertebral body during a hemi-vertebrectomy. Body 10 may be made from a metal, which may be a porous metal. The use of a porous metal enhances bony ingrowth. One example of such a material is Trabecular Metal™, which is marketed by Zimmer Spine, Inc., of Edina, Minn. Embodiments of this material are also described in several U.S. patents, including, for example, U.S. Pat. Nos. 5,443,515 and 6,063,042, each disclosure of which is expressly incorporated by reference herein in its entirety.

Implants 10 may be inserted by a variety of surgical approaches, including, but not limited to an anterior approach, a lateral (transverse) approach, a posterior approach, or postero-lateral approach by engaging the implant 10 with an instrument, such as an inserter. In the exemplary embodiment of implant 10 illustrated in FIGS. 1-7 and discussed above, openings 26 and 28 may be used to receive an inserter. However, in other embodiments, implant 10 may include grooves, indentations, slots or other surface deficits that allow the inserter to engage implant 10. For example, the trailing end 16 of body 12 of implant 10 may include holes, such as a circular hole or holes that mate with prongs on the inserter. Alternatively, body 12 may include two or more square or rectangular surface deficits cut into the superior 22 and inferior 24 surfaces proximate trailing end 16 that may be engaged by the inserter. In other embodiments, slots or grooves may be formed in each of the sides 18, 20. The slots or grooves may be partially formed into and engaged at the trailing end 16 by the inserter. The slots or grooves may be formed such that a portion of the implant 10 forms a positive stop for the inserter instrument. Alternatively, the slots or grooves may extend the length of the sides 18, 20 of body 12.

While the present invention has been illustrated by the description of and exemplary embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicants' general inventive concept.

What is claimed:

1. A spinal implant comprising:

a porous body comprising a leading end, a trailing end, a superior surface and an inferior surface, the porous body having a leading portion and a trailing portion defined by a midline dividing a length of the body in half; and the body defining only a single internal void, the void being a T-shaped void in the porous body, the T-shaped void defined by a first portion extending from a single opening in the trailing end to a location within the trailing portion, and a second portion extending from the first portion toward a single opening in the superior surface and toward a single opening in the inferior surface, the entire T-shaped void located only within the trailing portion.

2. The implant of claim 1, wherein the first portion of the void has a height and a width, wherein the height is smaller than the width, wherein the first and second portions of the void are configured for receipt of an inserter instrument to insert the implant between vertebral bodies.

3. The implant of claim 1, wherein the trailing end is convex.

4. The implant of claim 1, wherein the inferior surface has a generally trapezoidal shape.

5. The implant of claim 1, wherein the superior surface is generally dome-shaped, being convex between the leading and trailing ends and convex between first and second sides.

6. The implant of claim 1, wherein first and second sides of the porous body are generally straight and diverge away from one another from the leading end to the trailing end.

7. The implant of claim 1, wherein at least a portion of the leading end is generally straight.

8. The implant of claim 1, wherein the body is made of metal.

9. The implant of claim 1, wherein the leading end is a posterior end and the trailing end is an anterior end.

10. A spinal implant comprising:

a porous body comprising a leading end, a trailing end, a superior surface and an inferior surface, the porous body having a length extending between the leading end and a furthest point on the trailing end, the body having a leading portion and a trailing portion defined by a midline dividing the length in half, the body defining only two internal voids;

a first internal void located entirely within the trailing portion, the first void defined by only a single opening in the superior surface and only a single opening in the inferior surface; and a second internal void located entirely within the trailing portion, the second void defined by only a single opening communicating with the first void and only a single opening through the trailing end, the entire second void located only within the trailing portion, the first and second voids configured for receipt of an inserter instrument to insert the implant between vertebral bodies.

11. The implant of claim 10, wherein the trailing end is convex.

12. The implant of claim 10, wherein the superior surface is generally dome-shaped, being convex between the leading and trailing ends and convex between first and second sides.

13. The implant of claim 10, wherein the inferior surface has a generally trapezoidal shape.

14. The implant of claim 10, wherein first and second sides of the porous body are generally straight and diverge away from one another from the leading end to the trailing end.

15. The implant of claim 10, wherein the body is made of metal.

16. A spinal implant comprising:

a porous body comprising a leading end, a trailing end, a superior surface, and an inferior surface, the body having only a single internal void, the void being a T-shaped void, the T-shaped void having only three openings:

a first opening through the superior surface;

a second opening through the inferior surface, wherein the superior and inferior surfaces each define a surface area of the body, the first and second openings occupying substantially less than half the surface area of each of the superior and inferior surfaces of the body; and a third opening through the trailing end;

wherein the void is configured for receipt of an inserter instrument to insert the implant between vertebral bodies, wherein the body has a length extending between the leading end and a furthest point on the trailing end, the body having a leading portion and a trailing portion defined by a midline dividing the length in half, the entire void located only within the trailing portion.

17. The implant of claim 16, wherein the superior surface is generally dome-shaped, being convex between the leading and trailing ends and convex between first and second sides of the porous body.

18. The implant of claim 16, wherein the inferior surface has a generally trapezoidal shape.

19. The implant of claim 16, wherein the trailing end is convex and first and second sides of the porous body are generally straight and diverge away from one another from the leading end to the trailing end.

20. The implant of claim 16, wherein the body is made of metal.

* * * * *